US007833330B2

(12) United States Patent
Fronabarger et al.

(10) Patent No.: US 7,833,330 B2
(45) Date of Patent: Nov. 16, 2010

(54) LEAD-FREE PRIMARY EXPLOSIVE COMPOSITION AND METHOD OF PREPARATION

(75) Inventors: John W. Fronabarger, Phoenix, AZ (US); Michael D. Williams, Gilbert, AZ (US); William B. Sanborn, Chandler, AZ (US)

(73) Assignee: Pacific Scientific Energetic Materials Company, Chandler, AZ (US)

( * ) Notice: Subject to any disclaimer, the term of this patent is extended or adjusted under 35 U.S.C. 154(b) by 400 days.

(21) Appl. No.: 11/676,846

(22) Filed: Feb. 20, 2007

(65) Prior Publication Data

US 2009/0069566 A1 Mar. 12, 2009

Related U.S. Application Data

(60) Provisional application No. 60/800,816, filed on May 16, 2006.

(51) Int. Cl.
*H01B 1/16* (2006.01)
*C07D 257/04* (2006.01)
(52) U.S. Cl. ..................... 106/1.13; 548/250
(58) Field of Classification Search .............. 548/250
See application file for complete search history.

(56) References Cited

U.S. PATENT DOCUMENTS

| | | | |
|---|---|---|---|
| 2,066,954 A | 1/1937 | Herz | |
| 2,480,141 A | 8/1949 | King | |
| 3,351,015 A | 11/1967 | Wallack | |
| 3,486,453 A | 12/1969 | Smallwood | |
| 3,634,510 A | 1/1972 | Schmerling | |
| 3,791,301 A | 2/1974 | La Costa | |
| 4,093,623 A * | 6/1978 | Gilligan et al. | |
| 4,094,879 A * | 6/1978 | Bates et al. | |
| 4,133,707 A | 1/1979 | Andrew | |
| 5,417,160 A | 5/1995 | Mei et al. | |
| 5,610,367 A | 3/1997 | Erickson et al. | |
| 5,717,159 A | 2/1998 | Dixon et al. | |
| 5,831,208 A | 11/1998 | Erickson | |
| 6,478,903 B1 | 11/2002 | John, Jr. et al. | |
| 7,056,401 B2 | 6/2006 | Galluzzi | |
| 2006/0030715 A1 | 2/2006 | Hiskey et al. | |
| 2009/0223401 A1 | 9/2009 | Fronabarger et al. | |

FOREIGN PATENT DOCUMENTS

| | | |
|---|---|---|
| EP | 0941180 | 9/1999 |
| GB | 1106277 | 3/1968 |
| WO | WO-9711926 | 4/1997 |
| WO | WO-9902470 | 1/1999 |
| WO | WO9944965 | 9/1999 |
| WO | WO2008048351 | 4/2008 |
| WO | WO-2009/114347 | 9/2009 |

OTHER PUBLICATIONS

Talawar et al., J. Hazardous Materials, A120, 2005, 25-35, especially p. 26.*
Patani et al., Chem Rev, 1996, vol. 96 (8), especially p. 3148.*
Barsan & Miller, Health Hazard Evaluation Report, HETA Report #91-0346-2572, FBI Academy, Quantico, Virginia, pp. ii-iv and 1-33 (Apr. 1996).
Qualification and Final (Type) Qualification Procedures for Navy Explosives, Naval Sea Systems Command Instruction #8020.5C, ("NAVSEAINST 8020.5C"), 40 pages (May 5, 2000).
Fourth Report on the Investigation of the Alternatives to Lead Azide and Lead Styphnate, NSWC-IH contract #N00174-06-C-0079, pp. 1-23 (Sep. 20, 2007).
Molecular Basis for Secondary Flash Suppression, Hastie, J.W., Bonnell, D.W. and Schenck, P.K., U.S. Army Research Office, Document ARO 18375-CH, MIPR 102-84, 26 pages (Jul. 1, 1986).
International Search Report and Written Opinion in related International Application No. PCT/US07/04846.
International Search Report and Written Opinion dated Sep. 2, 2009 in related Application No. PCT/US2009/035952
Fronabarger, J W et al., "Preparation characterization and output testing of salts of, 7-hydroxy-4,6-dinitrobenzofuroxan" Safe Journal Spring 2007 Survival and Flight Equipment Association (SAFE) US, vol. 35, No. 1, Apr. 2007, pp. 14-18, XP008110604 1, Apr. 2007.*
Spear, R J et al., "Structure and Properties of the Potassium Hydroxide-Dinitrobenzofuro XAN Adduct (KDNBF) and Related Explosive Salts." Propellants, Explosives, Pyrotechnics, vol. 8, No. XP008110603 3, Jun. 1983, 85-88.*

* cited by examiner

*Primary Examiner*—Susannah Chung
(74) *Attorney, Agent, or Firm*—Dean W. Russell; Tiffany L. Williams; Kilpatrick Stockton LLP

(57) ABSTRACT

Embodiments of the present subject matter provide a compound and material that may be used as a lead-free primary explosive. An embodiment of the present subject matter provides the compound copper(I) nitrotetrazolate. Certain embodiments of the present subject matter provide methods for preparing lead-free primary explosives. The method includes: providing cuprous salt; providing water; providing 5-nitrotetrazolate salt; combining the cuprous salt, water and 5-nitrotetrazolate salt to form a mixture; and heating the mixture. The method may also include providing cuprous chloride and providing sodium 5-nitrotetrazolate. Certain embodiments of the present subject matter also provide methods for preparing copper(I) nitrotetrazolate. The method includes: providing cuprous salt; providing water; providing 5-nitrotetrazolate salt; combining the cuprous salt, water and 5-nitrotetrazolate salt to form a mixture; and heating the mixture. The method may also include providing cuprous chloride and providing sodium 5-nitrotetrazolate.

7 Claims, 7 Drawing Sheets

```
Peak Table
Peak Style              Peaks and Valleys
Peak Threshold          0.0100
Range                   800.000nm to 200.000nm Wavelength (nm)    Abs        Type
    256.000        0.650        P
    232.000        0.513        V
```

LEAD-FREE PRIMARY EXPLOSIVE COMPOSITION AND METHOD OF PREPARATION

CROSS-REFERENCE TO RELATED APPLICATIONS

The present application is related to and claims priority benefits from U.S. Provisional Patent Application Ser. No. 60/800,816 filed on May 16, 2006, entitled LEAD-FREE PRIMARY EXPLOSIVE COMPOSITION AND METHOD OF PREPARATION. The '816 application is hereby incorporated by reference herein in its entirety.

FIELD OF THE INVENTION

This invention relates to explosives, and in particular to primary explosives that are free of lead.

BACKGROUND OF THE INVENTION

Explosive materials have a wide variety of applications. Primary explosives are sensitive explosive materials that are used, in relatively small quantities, to initiate a secondary or main explosive charge. Primary explosives should be sufficiently sensitive to be detonated reliably but not so sensitive as to be exceedingly dangerous to handle. Moreover, primary explosives should have sufficient thermal stability so as to not decompose on extended storage or temperature fluctuation. Many primary explosives in current use contain lead, with the most well-known example being lead azide. These lead-containing explosives are undesirable from an environmental standpoint, since their use and manufacture can contribute to or cause lead contamination.

Thus, there is a need in the art for lead-free explosive materials and in particular for lead-free primary explosives. Certain lead-free primary explosives have been proposed. For instance, nitrotetrazole-based primary explosives have been proposed in U.S. Pat. Nos. 4,093,623 and 4,094,879, as well as in U.S. Patent App. Pub. No. 2006/0030715. For a variety of reasons, some of these proposed compounds have failed to serve as commercially viable substitutes for lead-containing primary explosives, while others exhibit characteristics that make them undesirable for at least some commercial applications. For example, U.S. Patent App. Pub. No. 2006/0030715 discloses certain nitrotetrazole complexes (including copper(II) complexes) which form a crystalline structure that is difficult to work with from a handling and ordinance loading standpoint.

SUMMARY OF THE INVENTION

Certain embodiments of the present subject matter are directed to a compound and material that may be used as a lead-free primary explosive, and methods for preparing such compound and material.

A first aspect of the present subject matter is the compound copper(I) nitrotetrazolate.

Another aspect of the present subject matter is a compound prepared by the following steps: providing cuprous salt; providing water; providing 5-nitrotetrazolate salt; combining the cuprous salt, water and 5-nitrotetrazolate salt to form a mixture; and heating the mixture.

Another aspect of the present subject matter is a compound prepared by the following steps: providing cuprous chloride; providing water; providing sodium 5-nitrotetrazolate; combining the cuprous chloride, water and sodium 5-nitrotetrazolate to form a mixture; and heating the mixture.

Yet another aspect of the present subject matter is a method of preparing copper(I) nitrotetrazolate which consists of the steps of: providing cuprous salt; providing water; providing 5-nitrotetrazolate salt; combining the cuprous salt, water and 5-nitrotetrazolate salt to form a mixture; and heating the mixture.

Yet another aspect of the present subject matter is a method of preparing copper(I) nitrotetrazolate which consists of the steps of: providing cuprous chloride; providing water; providing sodium 5-nitrotetrazolate; combining the cuprous chloride, water and sodium 5-nitrotetrazolate to form a mixture; and heating the mixture.

A further aspect of the present subject matter is a method of preparing a lead-free primary explosive, comprising the steps of: providing cuprous salt; providing water; providing 5-nitrotetrazolate salt; combining the cuprous salt, water and 5-nitrotetrazolate salt to form a mixture; and heating the mixture.

A further aspect of the present subject matter is a method of preparing a lead-free primary explosive, comprising the steps of: providing cuprous chloride; providing water; providing sodium 5-nitrotetrazolate; combining the cuprous chloride, water and sodium 5-nitrotetrazolate to form a mixture; and heating the mixture.

Another aspect of the present subject matter is the reaction product of a cuprous salt and a 5-nitrotetrazolate salt in water.

Yet a further aspect of the present subject matter is the reaction product of cuprous chloride and sodium 5-nitrotetrazolate in water.

Another aspect of the present subject matter is a product prepared by the following steps: providing cuprous chloride; providing a solvent (which may be water); providing sodium 5-nitrotetrazolate; combining the cuprous chloride, solvent, and sodium 5-nitrotetrazolate to form a mixture; and heating the mixture.

Another aspect of the present subject matter is a product prepared by the following steps: providing cuprous chloride; providing a solvent (which may be water); providing sodium 5-nitrotetrazolate; providing hydrochloric acid; combining the cuprous chloride, solvent, sodium 5-nitrotetrazolate, and hydrochloric acid to form a mixture; and heating the mixture.

Another aspect of the present subject matter is a compound prepared by the following steps: providing cuprous salt; providing water; providing 5-nitrotetrazolate salt; providing hydrochloric acid; combining the cuprous salt, water, 5-nitrotetrazolate salt, and hydrochloric acid to form a mixture; and heating the mixture.

Yet another aspect of the present subject matter is a method of preparing copper(I) nitrotetrazolate which consists of the steps of: providing cuprous salt; providing water; providing 5-nitrotetrazolate salt; providing hydrochloric acid; combining the cuprous salt, water, 5-nitrotetrazolate salt, and hydrochloric acid to form a mixture; and heating the mixture.

Another aspect of the present subject matter is a method of preparing copper(I) nitrotetrazolate which consists of the steps of: providing copper(I) ions; providing 5-nitrotetrazolate ions; providing a solvent; combining the copper(I) ions, 5-nitrotetrazolate ions, and solvent to form a mixture; and heating the mixture. Another aspect of the present subject matter is a compound prepared by the above steps.

The foregoing description of aspects of the present subject matter has been presented for purposes of illustration and description. Other aspects of the subject matter will be apparent to persons familiar with the present subject matter.

DETAILED DESCRIPTION OF THE INVENTION

Figure 1:
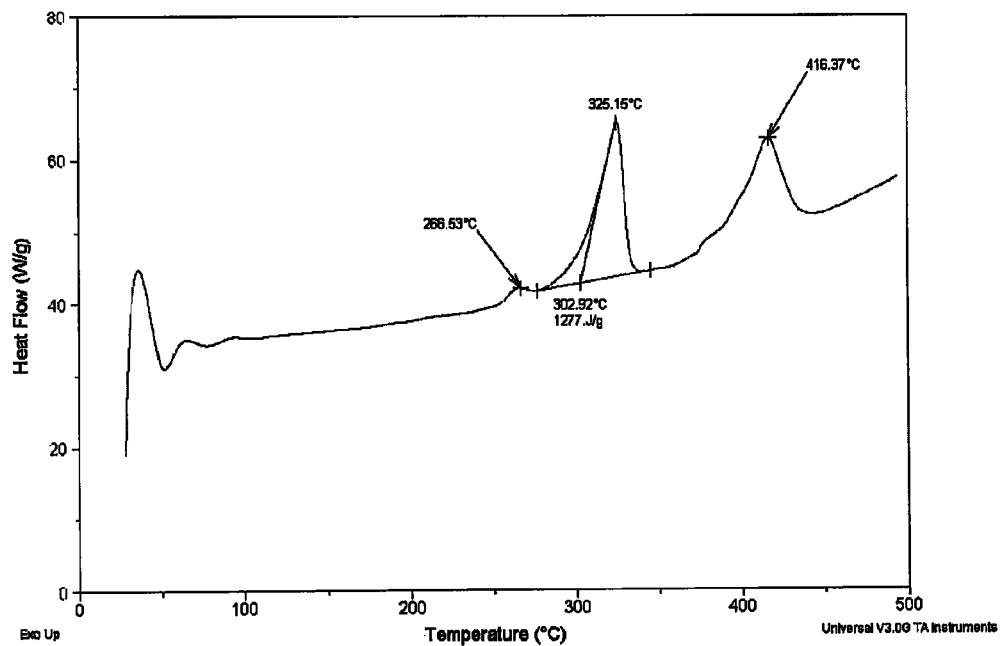
FIG. 1 shows the results of a differential scanning calorimetry (DSC) analysis on a material prepared according to the present techniques.

One aspect of the present subject matter is the compound copper(I) nitrotetrazolate. Copper(I) nitrotetrazolate has two possible isomers, both of which are contemplated herein. The isomers are depicted below:

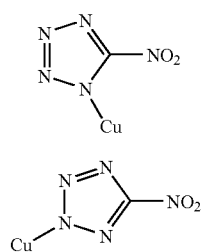

Alternatively, isomer (I) is contemplated. Alternatively, isomer (II) is contemplated. As yet another alternative, a mixture of isomers (I) and (II) is contemplated. Applicants note that USAARADC Technical Report ARBRL-TR-02371 (Schroeder and Henry) suggests that 1-substituted tetrazoles are more stable than 2-substituted tetrazoles. Also contemplated is any mixture which contains copper(I) nitrotetrazolate in a significant quantity (e.g. greater than about 1 weight percent, or alternatively, greater than about 5 weight percent).

Methods for preparing copper(I) nitrotetrazolate are contemplated in the present application. Copper(I) nitrotetrazolate may be prepared by reacting a copper(I) salt (for example, cuprous chloride) and a 5-nitrotetrazolate salt (for example, sodium 5-nitrotetrazolate) in a solvent (for example, water). Any suitable copper(I) salt, or combination of copper(I) salts, may be employed. Suitable copper(I) salts include, but are not limited to, cuprous chloride and cuprous bromide. Alternatively, cuprous chloride may be used as the copper(I) salt. Likewise, any suitable 5-nitrotetrazolate salt, or combination of 5-nitrotetrazolate salts, may be employed. Suitable 5-nitrotetrazolate salts include, but are not limited to, sodium 5-nitrotetrazolate and potassium 5-nitrotetrazolate. Likewise, any suitable solvent, or combination of solvents, may be employed. Suitable solvents include, but are not limited to, water, dimethyl sulfoxide (DMSO), as well as other polar organic solvents. Optionally, an acid (for example, hydrochloric acid) may be added to the reaction described above. Suitable acids include, but are not limited to, nitric acid, sulfuric acid, perchloric acid, and acetic acid. Alternatively, hydrochloric acid may be used.

It will be understood that ionic versions of the salts referred to above may be employed in the preparation of copper(I) nitrotetrazolate. In other words, copper(I) nitrotetrazolate may be prepared by a reaction in which copper(I) ions and 5-nitrotetrazolate ions are combined to form copper(I) nitrotetrazolate. By way of non-limiting example, a copper(I) salt may be reacted with 5-nitrotetrazolate ions to form copper(I) nitrotetrazolate.

The components may be reacted under conditions suitable to synthesize copper(I) nitrotetrazolate. Alternatively, the components may be reacted by mixing them together and then heating the mixture. The mixture may be heated in the temperature range of about 70° C. to about 150° C., alternatively in the temperature range of about 80° C. to about 130° C., alternatively to about 100° C. As yet another alternative, a reflux condenser may be employed, and the mixture may be heated to the reflux point. The duration of the heating or refluxing step may be a duration that is greater than about 5 minutes, alternatively greater than about 10 minutes, alternatively greater than about 20 minutes, alternatively from about 10 minutes to about 2 hours, alternatively from about 10 minutes to about 1 hour, alternatively about 15 minutes. Alternatively, the heating or refluxing step may be of sufficient duration such that the reaction goes to completion.

Regarding quantities of the components employed, 5-nitrotetrazolate may be supplied in a molar ratio of about 0.5 moles to about 4 moles 5-nitrotetrazolate per mole of copper (I). Alternatively, 5-nitrotetrazolate may be supplied in a molar ratio of about 0.8 moles to about 1.5 moles 5-nitrotetrazolate per mole of copper(I). Alternatively, 5-nitrotetrazolate may be supplied in a molar ratio of about 1 mole to about 1.2 moles 5-nitrotetrazolate per mole of copper(I). For example, sodium 5-nitrotetrazolate (NaNT) may be supplied in a molar ratio of about 0.5 moles to about 4 moles NaNT per mole of cuprous chloride, alternatively about 0.8 moles to about 1.5 moles NaNT per mole of cuprous chloride, alternatively about 1 mole to about 1.2 moles NaNT per mole of cuprous chloride.

A solvent may be supplied in an amount that is suitable to effectuate the reaction between 5-nitrotetrazolate and copper (I). For example, water (or other solvent) may be supplied in an amount that is suitable to effectuate the reaction between a 5-nitrotetrazolate salt and a copper(I) salt. As a more specific example, water (or other solvent) may be supplied in an amount that is suitable to effectuate the reaction between NaNT and cuprous chloride. Alternatively, water (or other solvent) may be supplied such that the concentration of 5-nitrotetrazolate salt in the reaction mixture would be in the range of about 0.01 M to about 2 M, alternatively in the range of about 0.05 M to about 0.5 M, alternatively about 0.3 M. For example, water may be supplied such that the concentration of NaNT in the reaction mixture would be in the range of about 0.01 M to about 2 M, alternatively in the range of about 0.05 M to about 0.5 M, alternatively about 0.3 M.

The addition of an acid to the reaction can improve the thermal stability of the resulting product. Thus an acid may be added to the reaction in a quantity that improves the thermal stability of the resulting product. Alternatively, the acid may be added to the reaction mixture in a molar ratio of about 0.1 moles to about 5 moles acid per mole of 5-nitrotetrazolate, alternatively in a molar ratio of about 0.5 moles to about 3 moles acid per mole of 5-nitrotetrazolate, alternatively in a molar ratio of about 1 mole acid per 1 mole 5-nitrotetrazolate. The acid added to the reaction may be hydrochloric acid, for example. Alternatively, nitric, sulfuric, perchloric, or acetic acid, or mixtures of foregoing (including hydrochloric acid), may be added. These exemplary acids are typically supplied in aqueous solution.

The reaction components may be combined in any order or sequence suitable to effectuate the reaction. By way of non-limiting example, the reaction of 5-nitrotetrazolate salt and copper(I) salt may be carried out by adding an aqueous solution of 5-nitrotetrazolate salt to an aqueous suspension of copper(I) salt, or vice versa. If such a reaction methodology is employed, the concentration of 5-nitrotetrazolate salt in the aqueous solution may be in the range of about 0.05 M to about 3 M, alternatively in the range of about 0.1 M to about 1 M, alternatively about 0.2 M to about 0.3 M, alternatively 0.28 M. The concentration of copper(I) salt in the aqueous suspension may be in the range of about 0.005 g/ml to about 2 g/ml, alternatively in the range of about 0.01 g/ml to about 1 g/ml, alternatively about 0.1 g/ml, alternatively about 0.02 g/ml. If the optional acid is employed, such acid may be added to either the 5-nitrotetrazolate salt solution or the copper(I) salt suspension prior to combination, or it may be added to the reaction mixture after combination (or it could be added in separate addition steps at more than one point). By way of non-limiting example, if acid is added to the 5-nitrotetrazolate salt solution prior to combination with the copper(I) salt suspension, it may be added in a molar ratio of about 0.1 moles to about 5 moles acid per mole of 5-nitrotetrazolate, alternatively in a molar ratio of about 0.5 moles to about 3 moles acid per mole of 5-nitrotetrazolate, alternatively in a molar ratio of about 1 mole acid per 1 mole 5-nitrotetrazolate.

The copper(I) nitrotetrazolate formed by the reaction of cuprous salt (for example, cuprous chloride), water and 5-nitrotetrazolate salt (for example, sodium 5-nitrotetrazolate) may be a precipitate. The precipitate may be separated by a suitable method known to those of skill in the art. Alternatively, the precipitate may be separated by filtration. As yet another alternative, the precipitate may be separated using a flotation technique. It may be desirable to separate finer or lighter precipitate particles from coarser or heavier precipitate particles (for example, the coarser or heavier particles may be desirable from the standpoint of easy handling and loading). A flotation technique may be employed to achieve such a separation, as may other techniques known to those of skill in the art. Alternatively, the fine particles may be removed by careful decanting. Alternatively, the precipitate (which may, for example, be a dark brown precipitate) is collected over filter paper.

The precipitate formed by the reaction of cuprous salt (for example, cuprous chloride), water and 5-nitrotetrazolate salt (for example, sodium 5-nitrotetrazolate) may be washed. For example, the product may be washed either a single time or multiple times with water. Alternatively, the product may be washed either a single time or multiple times with alcohol, for example, isopropanol. Alternatively, the product may be washed in multiple steps and in any order with both water and alcohol. For example, the product may be washed sequentially with water and then isopropanol. The product may then be dried. For example, the product may be air dried. Alternatively the product may be dried in an oven at 65 to 80° C.

The present application also contemplates products made by the methods described above. In other words, the present application contemplates products made by reacting cuprous salt (for example, cuprous chloride) and 5-nitrotetrazolate salt (for example, sodium 5-nitrotetrazolate) in water, under the conditions and component quantities described above. The present application also contemplates the reaction product of cuprous salt (for example, cuprous chloride), water and 5-nitrotetrazolate salt (for example, sodium 5-nitrotetrazolate) as described above.

The products contemplated and made by the methods of the present application (in at least some aspects of the present subject matter, copper(I) nitrotetrazolate) are free of lead and have been found suitable for use as explosives and, in particular, as primary explosives. Thus, the present application also contemplates methods for preparing compounds suitable for use as primary explosives, and explosive devices employing such compounds. Benefits include low cost, ease of preparation and low toxicity waste streams and health benefits associated with low lead materials in both military and commercial applications.

Figure 5:
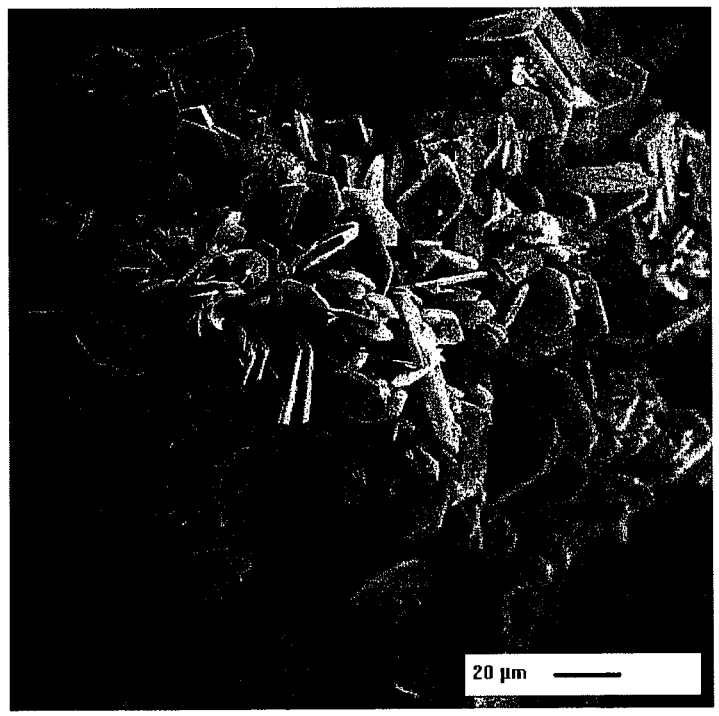
FIG. 5 is a Scanning Electron Microscopy (SEM) photomicrograph of a material prepared according to the present techniques.

The products contemplated and made by the methods of the present application (including copper(I) nitrotetrazolate) exhibit a crystalline structure that is suitable for loading and handling. A non-limiting example of such a crystalline structure is shown in FIG. 5 (Scanning Electron Microscopy (SEM) photomicrograph).

EXAMPLES

The following examples demonstrate the preparation and characterization of a material as taught herein.

Example 1

Copper(I) nitrotetrazolate was prepared as follows. Cuprous chloride (0.10 g) was suspended in 5 mL of water in a 25 mL Erlenmeyer flask under a nitrogen atmosphere. The mixture was heated to 90° C. on a hot plate with stirring. Sodium 5-nitrotetrazolate dihydrate (0.178 g) was dissolved in 5 mL of water and added to the flask using 2 mL of water to transfer. The solution was stirred at elevated temperature for 5 minutes at which point a small amount of brownish solid had formed. The mixture was stirred with heating for an additional 9 minutes and then the heating was suspended. The resulting brown solid was filtered over Millipore HVLP (0.45 μm) filter paper, washed twice with water, three times with isopropanol and then dried in a convection oven at 70° C.

Figure 2:
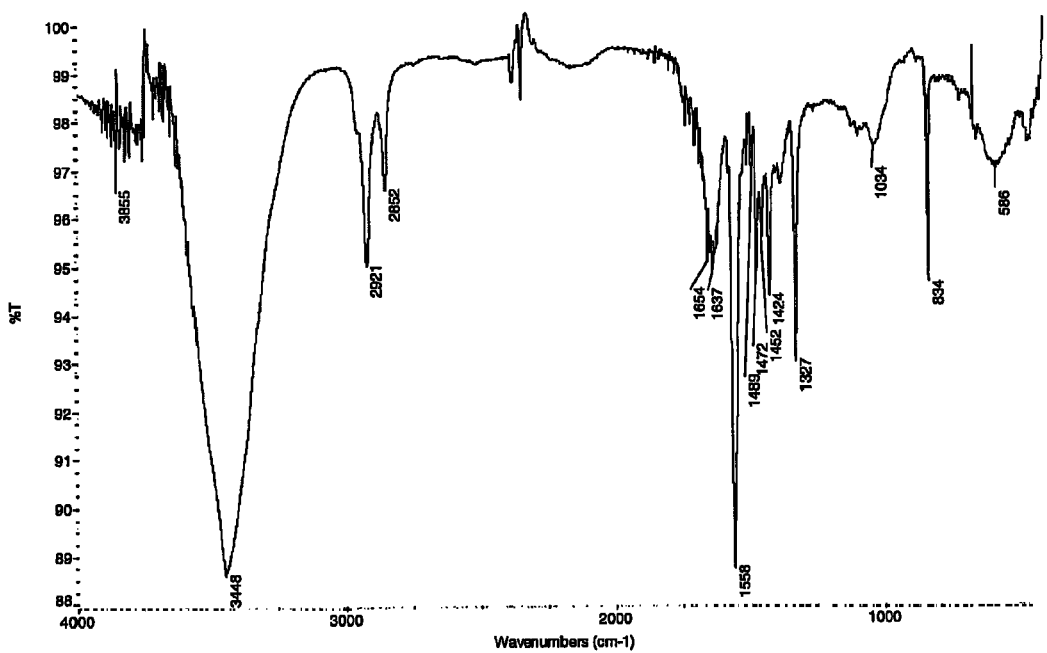
FIG. 2 shows the results of a Fourier Transform Infrared Spectroscopy (FTIR) analysis on a material prepared according to the present techniques.

The results of a differential scanning calorimetry (DSC) analysis on the solid are shown in FIG. 1. The results of a Fourier Transform Infrared Spectroscopy (FTIR) analysis on the solid are shown in FIG. 2.

Example 2

Copper(I) nitrotetrazolate was prepared as follows. Cuprous chloride (0.90 g, 9.01 mmol) was suspended in 20 mL of water in a 100 mL round bottom flask containing an oval magnetic stir bar. The flask was placed in an oil bath and controlled stirring was started at a rate of 600 RPM. Sodium 5-nitrotetrazolate dihydrate (2.08 g, 1.2 eq.) was dissolved in 20 mL of water and added to the flask. A reflux condenser was placed on the flask and the solution was heated to reflux (approximately 100° C.). The initially green solution turned brown during heating and a brown precipitate formed at or near reflux temperature. The solution was maintained at reflux for about 50 minutes. The flask was removed from the oil bath. The fine, light brown particles were removed by careful decanting and the remaining dark brown material was filtered over Whatman #1 filter paper. The dark brown product was washed three times with water and then three times with isopropanol and afforded a clear filtrate. The crystalline product (1.12 g) was air dried overnight.

Figure 3:
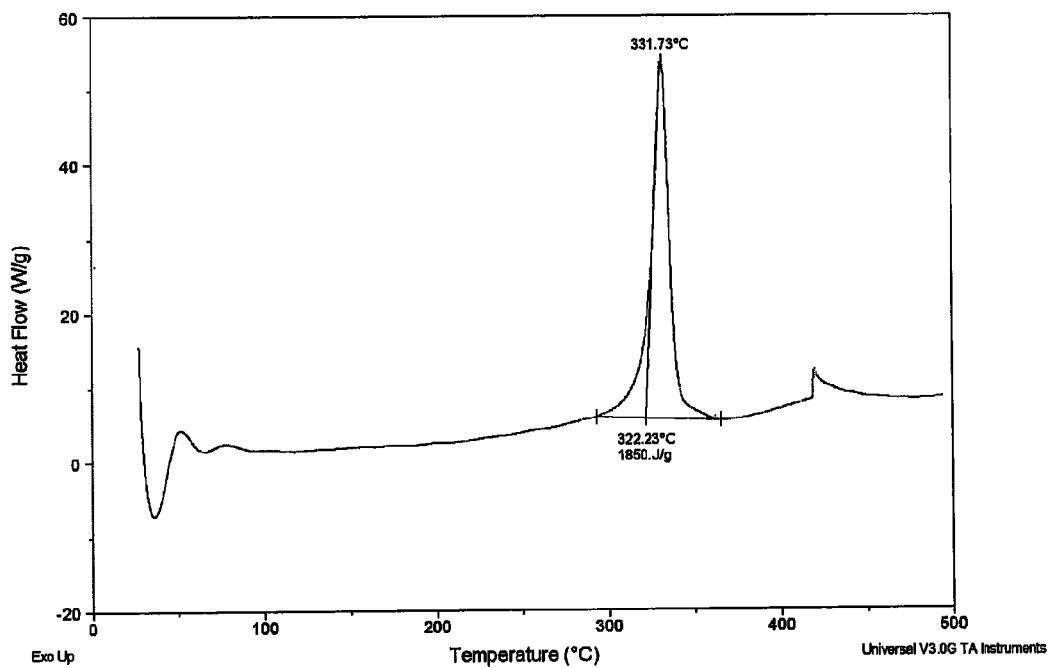
FIG. 3 shows the results of a DSC analysis on a material prepared according to the present techniques.
Figure 4:
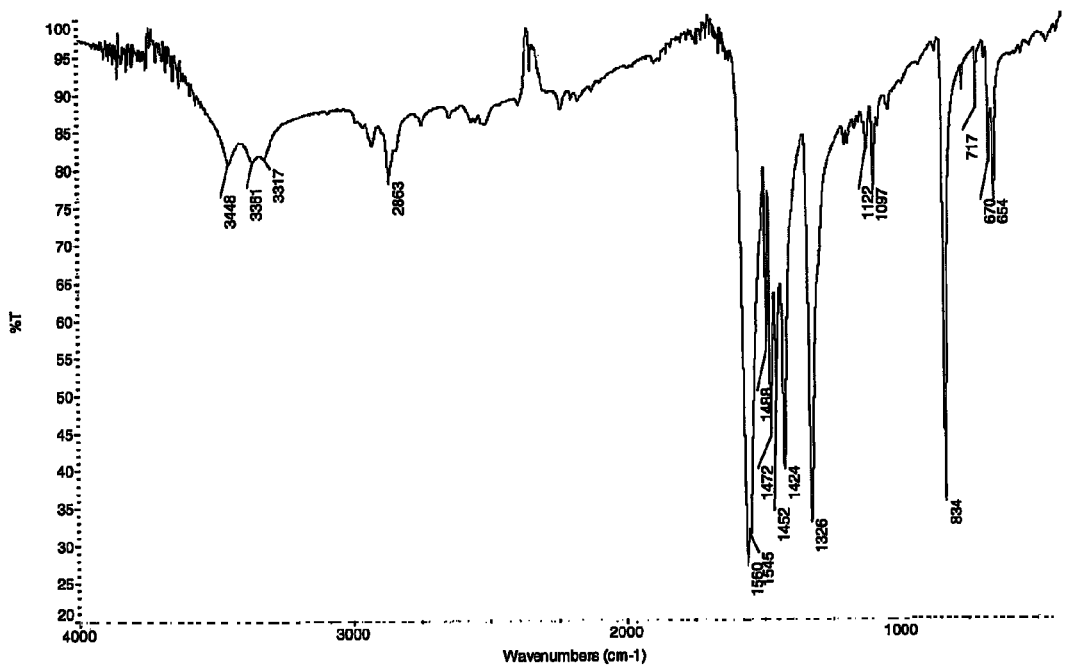
FIG. 4 shows the results of a FTIR analysis on a material prepared according to the present techniques.

The results of a differential scanning calorimetry (DSC) analysis on the crystalline product are shown in FIG. 3. The results of a Fourier Transform Infrared Spectroscopy (FTIR) analysis on the crystalline product are shown in FIG. 4. FIG. 5 is a Scanning Electron Microscopy (SEM) photomicrograph of the crystalline product.

The crystalline copper(I) nitrotetrazolate product was further dried in a convection oven at 65° C. for 4 hours and then stored in a dessicator before being subjected to several tests known to persons familiar with the field of technology. The results of these tests are as follows.

Friction Sensitivity Testing

Friction sensitivity testing was performed using a small scale Julius Peters BAM tester with a maximum load weight of 2075 g. Lead azide (a common lead-containing primary explosive) was also tested for purposes of comparison.

| | | |
|---|---|---|
| Copper(I) nitrotetrazolate | Low Fire Level: 10 g | No Fire Level: 0 g |
| Lead azide (RD1333) | Low Fire Level: 10 g | No Fire Level: 0 g |

Impact Sensitivity Testing

Impact sensitivity was tested using a ball drop instrument designed to meet the specifications of NATO AOP-7 registry number US/High Explosives/201.01.002. Lead azide was also tested for purposes of comparison.

| | |
|---|---|
| Copper(I) nitrotetrazolate | 0.040 ± 0.010 J |
| Lead azide (RD1333) | 0.050 ± 0.004 J |

Strong Confinement/Dent Block Testing

The test material and lead azide (RD1333) were both run (3 units per powder, 6 total) utilizing the following procedure for side by side comparison. ZPP (24 mg) was pressed into a header (P/N 2-300062) having a 1 ohm 0.0022" stablohm bridgwire at 10 kpsi. The materials were loaded into stainless steel cans having a 7 mil wall thickness and pressed at 10 kpsi. The headers were pressed into intimate contact with the output charges and sealed. The units were fired into 1" aluminum blocks and the resulting dents recorded.

| | | | |
|---|---|---|---|
| Copper(I) nitrotetrazolate | Avg. Dent: 0.037" | Avg. Function Time: 46 us |
| Lead azide (RD1333) | Avg. Dent: 0.033" | Avg. Function Time: 45 us |

As is evident from the above comparative testing, the material prepared according to the present techniques performed in a manner that is at least equivalent to lead azide.

Example 3

Copper(I) nitrotetrazolate was prepared as follows. Cuprous chloride (0.901 g, 9.01 mmol) was suspended in 20 mL of water in a 100 mL round bottom flask containing an oval magnetic stir bar. Sodium 5-nitrotetrazolate dihydrate (2.08 g, 1.2 eq.) was dissolved in 20 mL of water and added to the flask. A reflux condenser was placed on the flask and the solution was heated to reflux in a preheated (125° C.) oil bath. The stirring rate was maintained at 300 RPM. The initially dull green solution turned brown during heating and a brown precipitate formed at or near reflux temperature. The solution was maintained at reflux temperature for about 45 minutes. The flask was removed from the oil bath and the solids were allowed to settle. The flask was placed in a ring stand and suspended above a 1 L crystallizing dish. A glass tube (⅛") was connected to a DI water source using rubber tubing and the tube was inserted into the solids to the bottom the flask. DI water was introduced into the flask at such a flow rate as to suspend fine particles of the precipitate. These were decanted into the crystallizing dish by continuous DI water flow. Larger particles of the precipitate remained at the bottom of the round bottom flask. The remaining larger particles (a dark brown material) were filtered over Whatman #1 filter paper. The product was transferred with water and then washed three times with isopropanol and afforded a clear filtrate. The crystalline copper(I) nitrotetrazolate product (0.87 g) was air dried overnight before being subjected to several analyses known to persons familiar with the field of technology. The results of these analyses are as follows.

Figure 6:
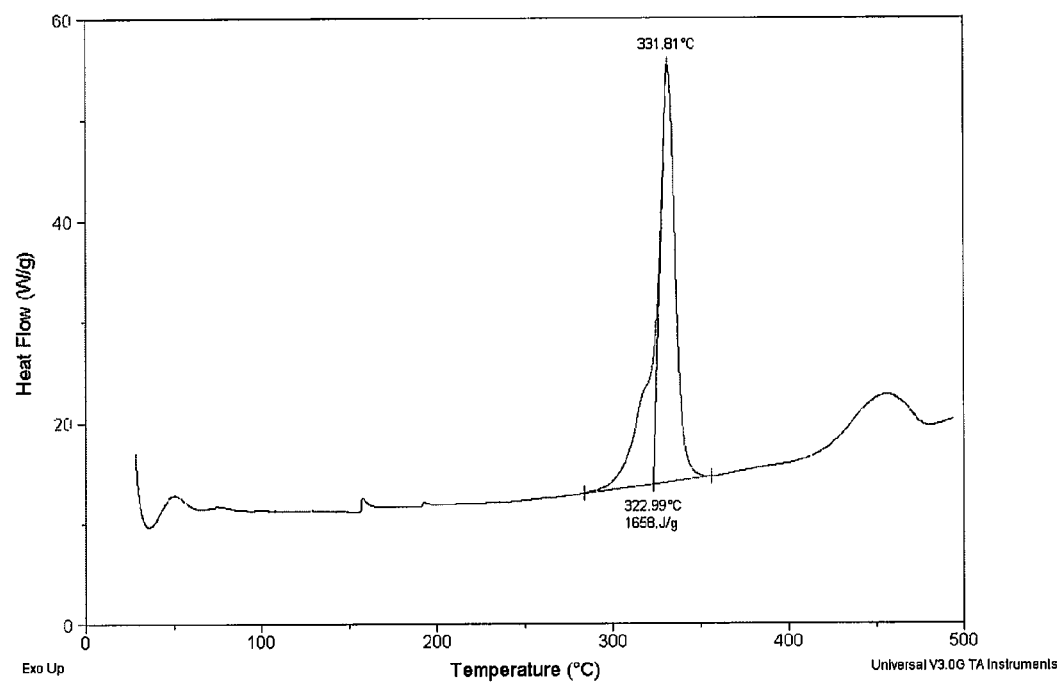
FIG. 6 shows the results of a DSC analysis on a material prepared according to the present techniques.
Figure 7:
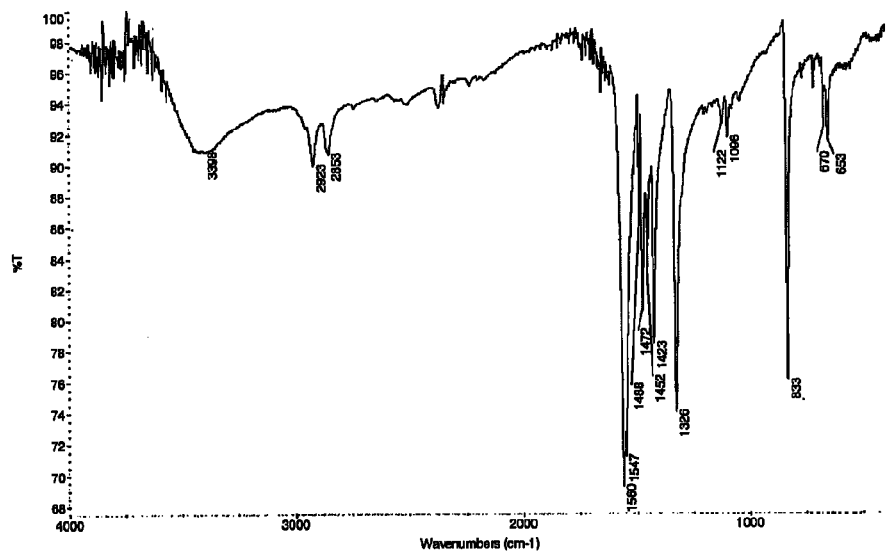
FIG. 7 shows the results of a FTIR analysis on a material prepared according to the present techniques.

The results of a differential scanning calorimetry (DSC) analysis on the crystalline product are shown in FIG. 6. The results of a Fourier Transform Infrared Spectroscopy (FTIR) analysis on the crystalline product are shown in FIG. 7.

Figure 8:
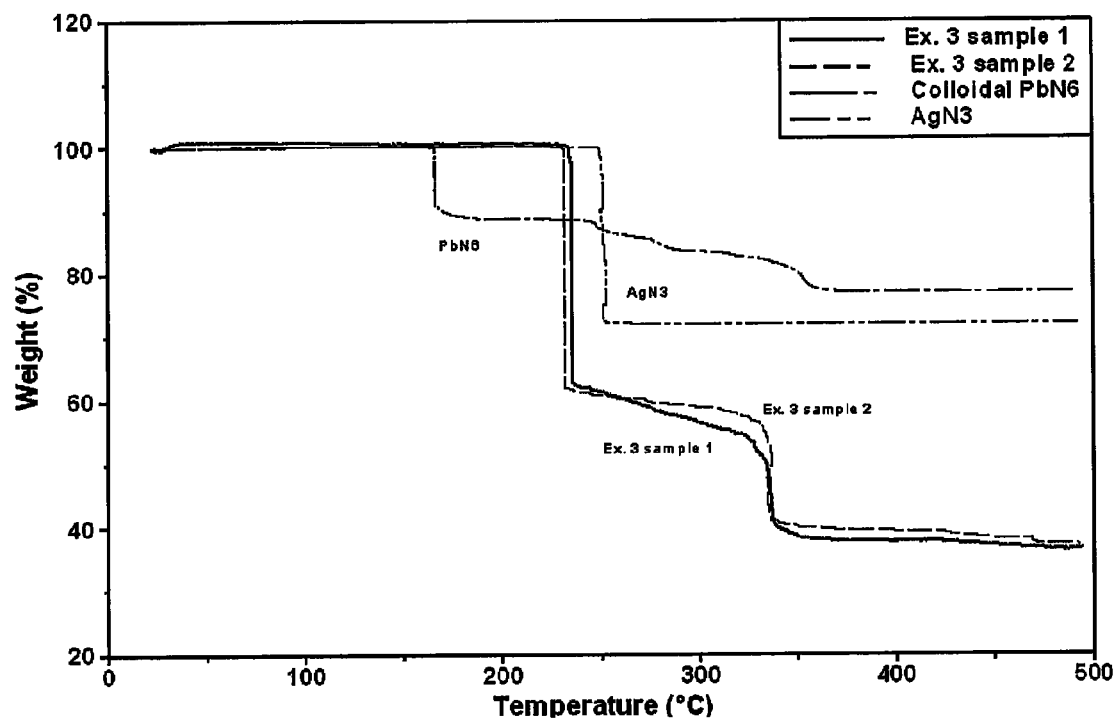
FIG. 8 shows the results of a Thermogravimetric Analysis (TGA) analysis on a material prepared according to the present techniques, as compared to silver and lead azide.

A Thermogravimetric Analysis (TGA) was conducted on samples of the crystalline product, as well as on comparative samples of colloidal lead azide and silver azide. The results of this analysis are shown in FIG. 8. The TGA analysis demonstrates the thermal stability of the crystalline product.

Figure 9:
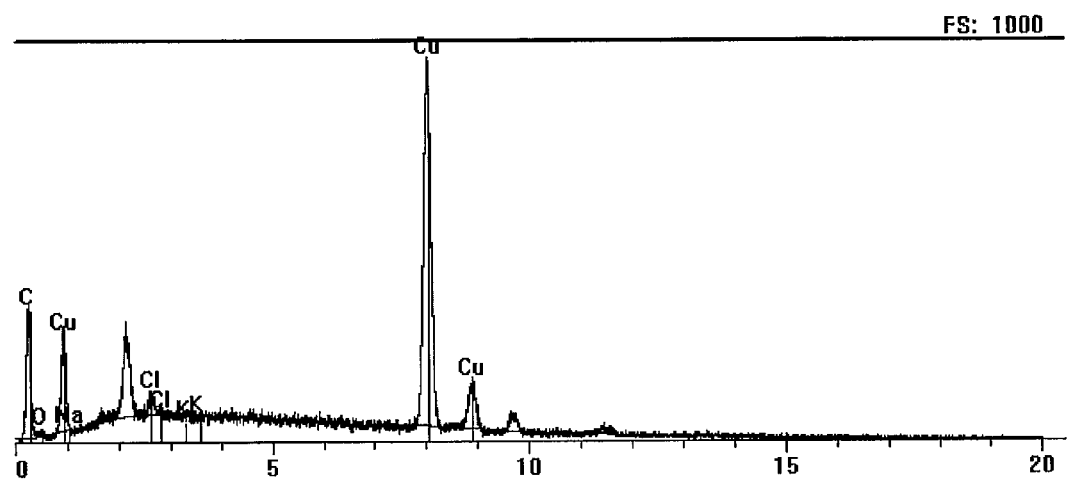
FIG. 9 shows the results of an energy dispersive spectroscopy analysis on a material prepared according to the present techniques.

Analysis by energy dispersive spectroscopy (EDS) was conducted on the crystalline product. The results of this semi-quantitative analysis are shown in FIG. 9 and as follows:

| Element | Line | keV | Kratio | Wt % | At % | ChiSquare |
|---|---|---|---|---|---|---|
| Na | KA1 | 1.041 | 0.0002 | 0.08 | 0.06 | 2.91 |
| K | KA1 | 3.313 | 0.0000 | 0.00 | 0.00 | 0.00 |
| Cu | KA1 | 8.046 | 0.2773 | 35.01 | 9.32 | 1.07 |
| Cl | KA1 | 2.622 | 0.0035 | 0.45 | 0.22 | 1.31 |
| C | KA1 | 0.277 | 0.1613 | 63.31 | 89.19 | 12.95 |
| O | KA1 | 0.523 | 0.0018 | 1.14 | 1.21 | 2.17 |
| Total | | | | 100.00 | 100.00 | 7.61 |

| Element | Line | Gross (cps) | BKG (cps) | Overlap (cps) | Net (cps) |
|---|---|---|---|---|---|
| Na | KA1 | 9.104 | 4.602 | 4.115 | 0.411 |
| K | KA1 | 13.177 | 13.438 | 0.000 | 0.000 |
| Cu | KA1 | 180.268 | 9.876 | 0.000 | 169.765 |

-continued

| | | | | | |
|---|---|---|---|---|---|
| Cl | KA1 | 19.222 | 12.700 | 0.000 | 6.661 |
| C | KA1 | 34.941 | 1.550 | 0.000 | 33.025 |
| O | KA1 | 3.428 | 2.274 | 0.000 | 1.174 |

| Element | Line | Det Eff | Z Corr | A Corr | F Corr | Tot Corr | Modes |
|---|---|---|---|---|---|---|---|
| Na | KA1 | 0.619 | 1.057 | 3.667 | 1.000 | 3.878 | Elmnt. |
| K | KA1 | 0.871 | 1.127 | 1.049 | 0.995 | 1.177 | Elmnt. |
| Cu | KA1 | 0.993 | 1.276 | 0.989 | 1.000 | 1.262 | Elmnt. |
| Cl | KA1 | 0.812 | 1.125 | 1.144 | 0.999 | 1.285 | Elmnt. |
| C | KA1 | 0.052 | 0.912 | 4.304 | 1.000 | 3.924 | Elmnt. |
| O | KA1 | 0.185 | 0.958 | 6.779 | 0.999 | 6.494 | Elmnt. |

The results of the energy dispersive spectroscopy analysis show that the crystalline product does not contain significant amounts of sodium, which would have indicated the presence of a copper complex (such as $Na_2Cu(NT)_4(H_2O)_2$ disclosed in U.S. Application Pub. No. 2006/0030715).

Analysis by ultraviolet spectrophotometry was conducted on the crystalline product. A weighted sample of the product was digested in 1N sodium hydroxide and filtered to remove the copper oxide. The rust color of this residue indicated that it was copper(I) oxide and not other copper oxides. The absorbance of the appropriately diluted filtrate was determined at 256 nanometers and the 5-nitrotetrazolate content determined using the following previously developed relationship:

$$Y=5243.4X-0.0098$$

Where:
$Y$=absorbance at 256 nanometers
$X$=concentration of sodium 5-nitrotetrazolate (moles/liter)

Figure 10:
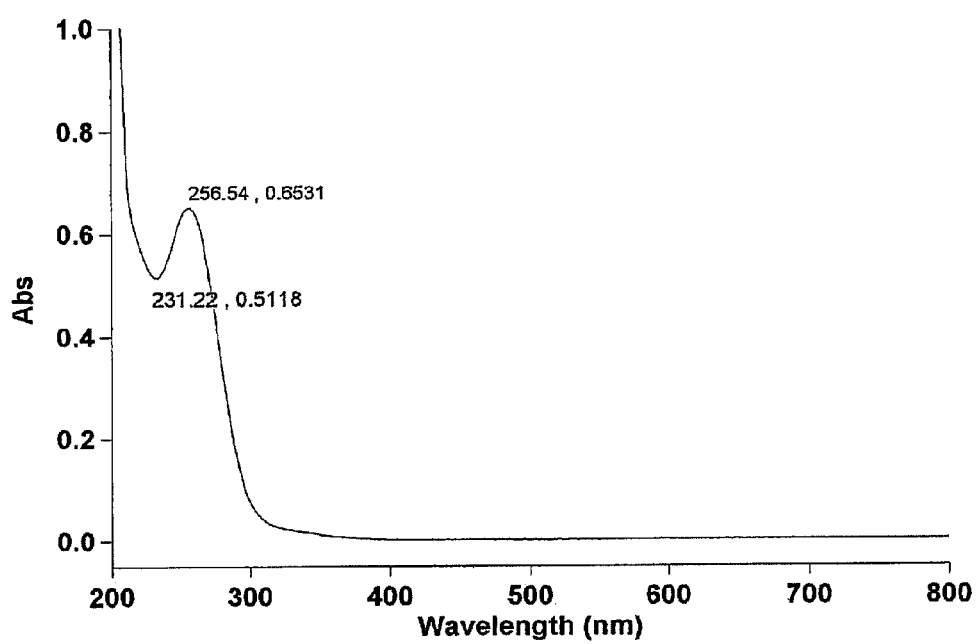
FIG. 10 shows the spectra resulting from an ultraviolet spectrophotometry analysis on a material prepared according to the present techniques.
Figures 11, 12:
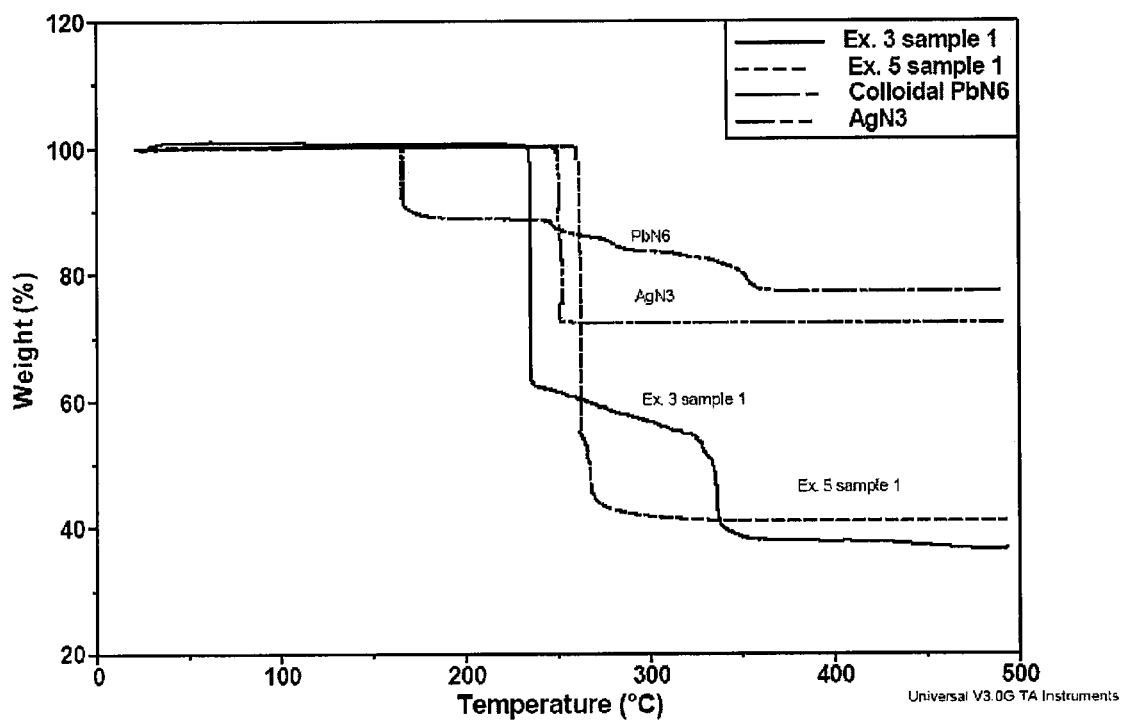
FIG. 11 shows the peak table for the ultraviolet spectrophotometry spectra shown in FIG. 10.
FIG. 12 shows the results of a TGA analysis on a material prepared according to the present techniques, as compared to silver and lead azide.

The UV spectrophotometry data is provided in FIGS. 10 and 11. The results demonstrate a 5-nitrotetrazolate content of 62.25% which compares well with the theoretical value of 64.22% for a copper to 5-nitrotetrazolate ratio of one-to-one.

The results of the above analyses demonstrate that the crystalline product is copper(I) nitrotetrazolate. In particular, the results of the energy dispersive spectroscopy analysis show that the crystalline product does not contain sodium or chlorine, while the results of the UV spectrophotometry demonstrate that copper (I) is present and that the copper and nitrotetrazole are present in a one-to-one ratio.

Example 4

Copper(I) nitrotetrazolate was prepared as follows. Cuprous chloride (0.45 g) was suspended in 20 mL of water in a 100 mL round bottom flask containing an oval magnetic stir bar. The flask was placed in a glycerin bath and controlled stirring was started at a rate of 300 RPM. Sodium 5-nitrotetrazolate dihydrate (0.98 g) was dissolved in 20 mL of water and added to the flask. A reflux condenser was placed on the flask and the solution was heated to reflux (approximately 100° C.). The initially green solution turned brown during heating and a brown precipitate formed at or near reflux temperature. The solution was maintained at reflux for about 34 minutes. The flask was removed from the glycerin bath. The fines were separated by decantation and water addition. The remaining precipitate was filtered over Whatman #1 filter paper. The dark brown product was washed three times with water and then three times with isopropanol and afforded a clear filtrate. The crystalline product was dried in an oven at 70° C.

Density testing was performed on the crystalline product. Density determined by helium pyncnometry was: 2.81±0.005 g/cc.

Example 5

Copper(I) nitrotetrazolate was prepared as follows. Cuprous chloride (0.454 g) was suspended in 5 mL of water in a 100 mL round bottom flask containing an oval magnetic stir bar under an argon atmosphere. The flask was placed in a glycerin bath and controlled stirring was started at a rate of 450 RPM. Sodium 5-nitrotetrazolate dihydrate (1.007 g) was dissolved in 16 mL of water and 6 mL of 1N HCl was added. The sodium 5-nitrotetrazolate solution was added to the flask. A reflux condenser was placed on the flask and the solution was heated to reflux (125° C. bath temperature). The initially light green solution turned rust brown during heating and a brown precipitate formed at or near reflux temperature. The solution was maintained at reflux for about 16 minutes. The flask was removed from the glycerin bath. The precipitate was collected over Whatman #1 filter paper. The dark brown product was washed five times with water and then three times with isopropanol and afforded a light green filtrate. The crystalline product was dried in an oven at 80° C. The yield of small rust crystals was 0.631 g.

A Thermal Gravimetric Analysis (TGA) was conducted on a sample of the crystalline product, as well as on comparative samples of colloidal lead azide and silver azide. The results of this analysis are shown in FIG. 12. The TGA analysis demonstrates the thermal stability of the copper(I) nitrotetrazolate and that it is superior to lead azide. The unusually low value for lead azide is undoubtedly due to the oxidation of lead azide to lead oxide via small impurities of oxygen present in the argon purge gas. This phenomenon is not seen in the copper(I) nitrotetrazolate or silver azide samples. The difference in TGA results for examples 3 and 5 are a direct result of the preparation of these materials. Example 5 employs dilute aqueous hydrochloric acid whereas example 3 uses only water in the preparation.

Figure 13:
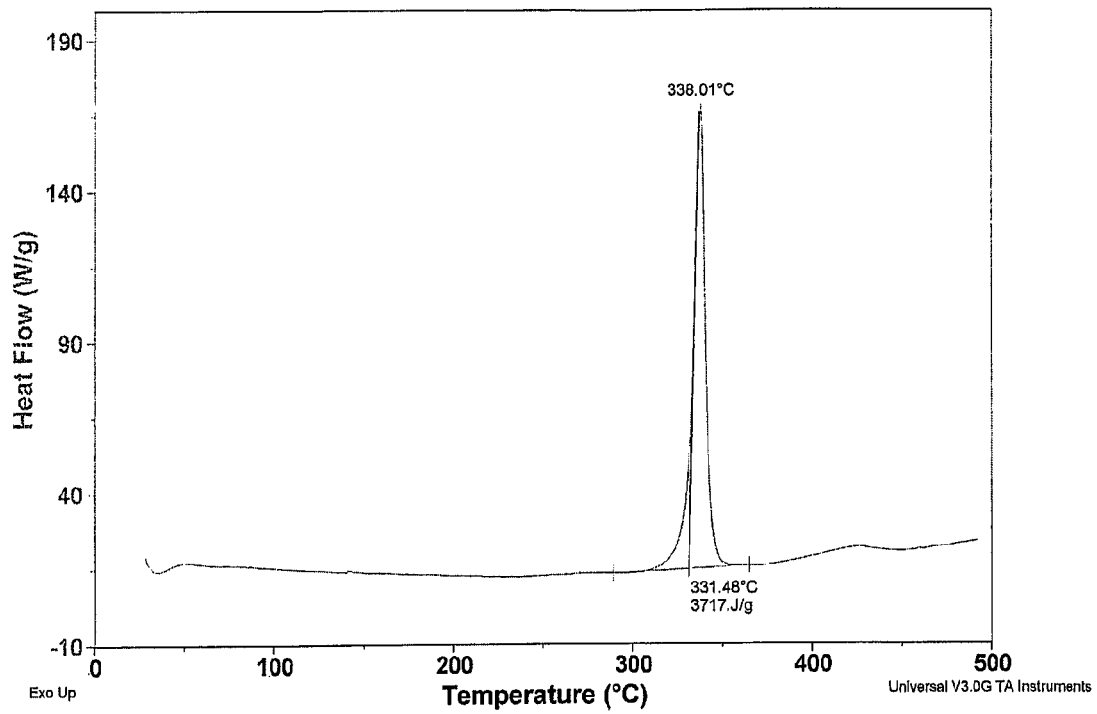
FIG. 13 shows the results of a DSC analysis on a material prepared according to the present techniques.
Figure 14:
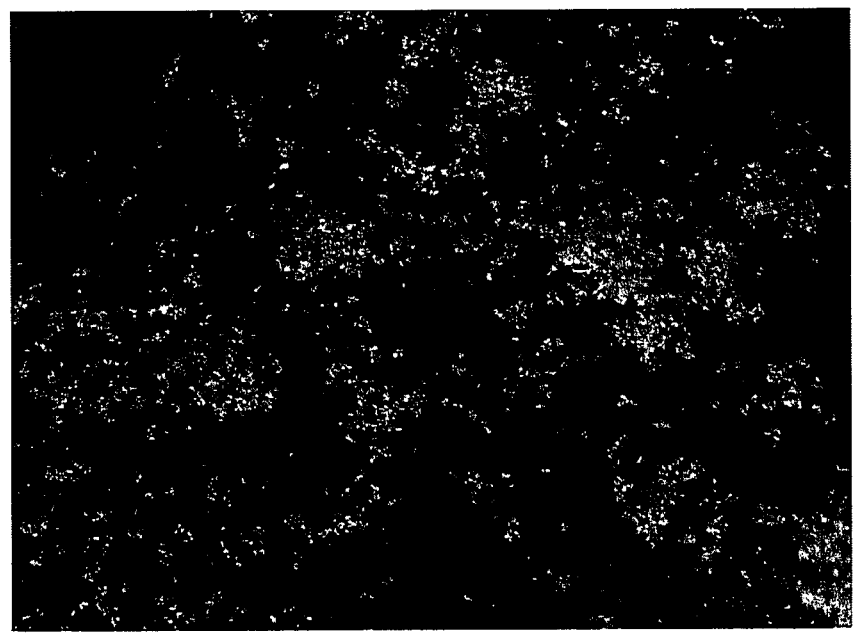
FIG. 14 shows an optical photomicrograph of a material prepared according to the present techniques.

The results of a differential scanning calorimetry (DSC) analysis on the crystalline product are shown in FIG. 13. FIG. 14 is an optical photomicrograph (80× magnification) of the product.

Example 6

A product is prepared as follows. Cuprous chloride (0.50 g) is suspended in water in a flask containing a magnetic stir bar. The flask is placed in a glycerin bath and controlled stirring is started. Sodium 5-nitrotetrazolate dihydrate (0.60 g) is dissolved in water and added to the flask. A reflux condenser is placed on the flask and the solution is heated to reflux (approximately 100° C.). The initially green solution turns brown during heating and a brown precipitate forms at or near reflux temperature. The solution is maintained at reflux for 15 minutes. The flask is removed from the glycerin bath. The fine particles are removed by careful decanting. The dark brown precipitate is washed multiple times with isopropanol. The product is then air dried.

Example 7

A product is prepared as follows. Cuprous chloride (0.83 g) is suspended in water. Sodium 5-nitrotetrazolate dihydrate (1.00 g) is dissolved in water. Hydrochloric acid (1N) is added to the sodium 5-nitrotetrazolate solution at a vol/vol ratio of 1:3. The sodium 5-nitrotetrazolate solution is added to the aqueous solution of cuprous chloride. A reflux condenser is placed on the flask and the solution is heated to reflux (approximately 100° C.). The initially green solution turns brown during heating and a brown precipitate forms at or near reflux temperature. The solution is maintained at reflux for about 30 minutes. The dark brown precipitate is collected over filter paper. The product is washed sequentially with water and isopropanol and then dried in an oven at 80° C.

Example 8

A product is prepared as follows. An aqueous solution of sodium 5-nitrotetrazolate (NaNT) and a suspension of cuprous chloride are combined such that the resulting molar ratio is about 1.2 moles NaNT per mole of cuprous chloride. The combined aqueous mixture is heated to reflux (approximately 100° C.). The initially green solution turns brown during heating and a brown precipitate forms at or near reflux temperature. The solution is maintained at reflux for up to 2 hours. The fine particles are removed by careful decanting. The dark brown product is washed multiple times with isopropanol. The product is dried in an oven at 70° C.

Example 9

A product is prepared as follows. An aqueous solution of sodium 5-nitrotetrazolate (NaNT) and a suspension of cuprous chloride are combined such that the resulting molar ratio is about 1 mole NaNT per mole of cuprous chloride. The combined aqueous mixture is heated to 90° C. The initially green solution turns brown during heating and a brown precipitate forms. The solution is heated for up to 2 hours. Upon removal from heat, the fine, light brown particles are removed, leaving a dark brown product. The dark brown precipitate is collected over filter paper. The dark brown product is washed sequentially with water and isopropanol. The product is then dried in an oven at 65° C.

Example 10

A product is prepared as follows. Cuprous chloride (1.00 g) is suspended in water under an argon atmosphere. Sodium 5-nitrotetrazolate dihydrate (3.48 g) is dissolved in water. Nitric acid (1N) is added to the sodium 5-nitrotetrazolate solution at a vol/vol ratio of 1:5. The sodium 5-nitrotetrazolate solution is added to the aqueous solution of cuprous chloride. The combined solution is heated to approximately 105° C. The initially green solution turns brown during heating and a brown precipitate forms. The solution is maintained at 105° C. for about 60 minutes. The flask is removed from heat. The fine particles are removed by careful decanting. The product is washed sequentially with water and isopropanol and then dried in an oven at 80° C.

Example 11

A product is prepared as follows. An aqueous solution of sodium 5-nitrotetrazolate (NaNT) and a suspension of cuprous chloride are combined such that the resulting molar ratio is about 0.85 moles NaNT per mole of cuprous chloride. The combined aqueous mixture is heated to 95° C. The initially green solution turns brown during heating and a brown precipitate forms. The solution is heated for up to 2 hours. Upon removal from heat, the fine, light brown particles are removed, leaving a dark brown product. The dark brown precipitate is collected over filter paper. The dark brown product is washed sequentially with water and isopropanol. The product is then dried in an oven at 80° C.

Example 12

A product is prepared as follows. Cuprous chloride (0.99 g) is suspended in water. Sodium 5-nitrotetrazolate dihydrate (1.73 g) is dissolved in water. The sodium 5-nitrotetrazolate solution is added to the flask containing the aqueous solution of cuprous chloride. The combined aqueous solution is heated to 100° C. The initially green solution turns brown during heating and a brown precipitate forms. The solution is heated for about 30 min. The resultant product is collected, washed with isopropanol, and dried.

Example 13

A product is prepared as follows. Cuprous chloride (0.50 g) is suspended in water in a flask containing a magnetic stir bar. The flask is placed in a glycerin bath and controlled stirring is started. Sodium 5-nitrotetrazolate dihydrate (0.93 g) is dissolved in water. Perchloric acid (0.1N) is added to the sodium 5-nitrotetrazolate solution at a vol/vol ratio of 1:5. The sodium 5-nitrotetrazolate solution is added to the flask containing the aqueous solution of cuprous chloride. The combined aqueous solution is heated to 105° C. The initially green solution turns brown during heating and a brown precipitate forms. The solution is heated for about 15 min. The flask is removed from the glycerin bath. The fine particles are removed by careful decanting. The dark brown precipitate is then collected over filter paper. The dark brown precipitate is washed multiple times with isopropanol. The product is then air dried.

Example 14

A product is prepared as follows. An aqueous solution of sodium 5-nitrotetrazolate (NaNT) and a suspension of cuprous chloride are combined such that the resulting molar ratio is about 0.8 moles NaNT per mole of cuprous chloride. The combined aqueous mixture is heated to approximately 110° C. The initially green solution turns brown during heating and a brown precipitate forms. The solution is heated for up to 2 hours. The resultant fine particles are removed by careful decanting. The resultant dark brown precipitate is collected over filter paper. The dark brown precipitate is washed sequentially with water and isopropanol and then dried in an oven at 80° C.

Example 15

A product is prepared as follows. Cuprous chloride (0.99 g) is suspended in water. Sodium 5-nitrotetrazolate dihydrate (1.73 g) is dissolved in water. Hydrochloric acid (1N) is added to the sodium 5-nitrotetrazolate solution at a vol/vol ratio of 1:4. The sodium 5-nitrotetrazolate solution is added to the aqueous solution of cuprous chloride. The solution is heated to approximately 100° C. The solution is heated for about 30 minutes. The resultant product is collected, washed with isopropanol, and dried.

Example 16

A product is prepared as follows. Cuprous chloride (0.50 g) is suspended in water in a flask containing a magnetic stir bar. The flask is placed in a glycerin bath and controlled stirring is started. Sodium 5-nitrotetrazolate dihydrate (1.05 g) is dissolved in water. Sulfuric acid (0.2N) is added to the sodium 5-nitrotetrazolate solution at a vol/vol ratio of 1:2. The sodium 5-nitrotetrazolate solution is added to the flask containing the aqueous solution of cuprous chloride. The solution is heated to approximately 85° C. The solution is heated for about 45 minutes. The flask is removed from the glycerin bath. The resulting product is collected, washed with isopropanol, and dried.

Example 17

A product is prepared as follows. An aqueous solution of sodium 5-nitrotetrazolate (NaNT) and a suspension of cuprous chloride are combined such that the resulting molar ratio is about 0.75 moles NaNT per mole of cuprous chloride. The combined aqueous mixture is heated to 125° C. for 25 min. Upon removal from heat, the fine, light brown particles are removed, leaving a dark brown product. The dark brown precipitate is collected over filter paper. The dark brown product is washed multiple times with isopropanol. The product is then dried in an oven at 80° C.

Example 18

A product is prepared as follows. An aqueous solution of sodium 5-nitrotetrazolate (NaNT) and a suspension of cuprous chloride are combined such that the resulting molar ratio is about 2 moles NaNT per mole of cuprous chloride. The combined aqueous mixture is heated to 115° C. for 90 min. Upon removal from heat, the dark brown precipitate is then collected over filter paper. The dark brown product is washed sequentially with water and isopropanol. The product is then dried in an oven at 80° C.

Example 19

A product is prepared as follows. Cuprous chloride (0.50 g) is suspended in water in a flask containing a magnetic stir bar under an argon atmosphere. The flask is placed in a glycerin bath and controlled stirring is started. Sodium 5-nitrotetrazolate dihydrate (1.04 g) is dissolved in water. Hydrochloric acid (0.1N) is added to the sodium 5-nitrotetrazolate solution at a vol/vol ratio of 1:1. The sodium 5-nitrotetrazolate solution is added to the flask containing the aqueous solution of cuprous chloride. The combined aqueous solution is heated to 90° C. for about 35 min. The flask is removed from the glycerin bath. The fine particles are removed by careful decanting and the dark brown precipitate is then collected over filter paper. The dark brown precipitate is washed multiple times with isopropanol. The product is then air dried.

All patents, test procedures, and other documents cited herein are fully incorporated by reference to the extent such disclosure is not inconsistent with the subject matter described and for all jurisdictions in which such incorporation is permitted.

While the present subject matter has been described and illustrated by reference to particular embodiments, it will be appreciated by those of ordinary skill in the art that the subject matter lends itself to many different variations not illustrated herein. For these reasons, then, reference should be made solely to the appended claims for purposes of determining the true scope of the present invention.

Although the appendant claims have single appendencies in accordance with U.S. patent practice, each of the features in any of the appendant claims can be combined with each of the features of other appendant claims or the main claim.

What is claimed is:

1. A compound consisting of copper(I) nitrotetrazolate, wherein copper(I) has one valence electron.

2. A compound having a formula selected from at least one member of the group consisting of isomers A and B, wherein each isomer comprises a copper ion with one valence electron:

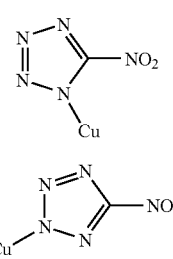

3. The compound of claim 1, wherein the compound is used as a replacement for lead azide.

4. The compound of claim 1 comprising a mixture of isomers (A) and (B), in which isomer (A) is:

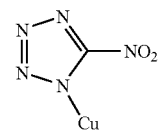

and isomer (B) is:

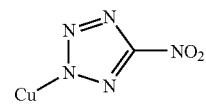

5. The compound of claim 4 in the form of a primary explosive.

6. The compound of claim 2, wherein the compound is used as a replacement for lead azide.

7. The compound of claim 2 in the form of a primary explosive.

* * * * *